US011273289B2

(12) United States Patent
Della Vecchia

(10) Patent No.: US 11,273,289 B2
(45) Date of Patent: Mar. 15, 2022

(54) VECTOR FLUSH SIZING CATHETER AND METHOD

(71) Applicant: Medtronic Vascular, Inc., Santa Rosa, CA (US)

(72) Inventor: Christopher J. Della Vecchia, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 250 days.

(21) Appl. No.: 16/353,370

(22) Filed: Mar. 14, 2019

(65) Prior Publication Data

US 2019/0314608 A1    Oct. 17, 2019

Related U.S. Application Data

(60) Provisional application No. 62/655,893, filed on Apr. 11, 2018.

(51) Int. Cl.
| | | |
|---|---|---|
| *A61M 25/01* | (2006.01) | |
| *A61F 2/954* | (2013.01) | |
| *A61M 25/00* | (2006.01) | |
| *A61M 5/00* | (2006.01) | |
| *A61F 2/07* | (2013.01) | |

(Continued)

(52) U.S. Cl.
CPC ............ *A61M 25/0136* (2013.01); *A61F 2/07* (2013.01); *A61F 2/954* (2013.01); *A61M 5/007* (2013.01); *A61M 25/007* (2013.01); *A61M 25/0108* (2013.01); *A61F 2/9517* (2020.05); *A61F 2002/065* (2013.01)

(58) Field of Classification Search
CPC .............. A61M 5/007; A61M 25/0138; A61M 25/0141; A61M 25/0144; A61M 25/0147; A61M 25/0152; A61M 25/0155; A61M 25/0133; A61M 25/0136; A61M 25/0108; A61B 17/12113; A61B 2090/3966
See application file for complete search history.

(56) References Cited

U.S. PATENT DOCUMENTS

| | | | |
|---|---|---|---|
| 4,279,252 A | | 7/1981 | Martin |
| 5,824,055 A | * | 10/1998 | Spiridigliozzi ......... A61F 2/954 623/1.11 |
| 6,730,119 B1 | | 5/2004 | Smalling |
| (Continued) | | | |

FOREIGN PATENT DOCUMENTS

| | | |
|---|---|---|
| CN | 102791321 A | 11/2012 |
| EP | 1943974 A1 | 7/2008 |

OTHER PUBLICATIONS

PCT/US2019/022244, The International Search Report and the Written Opinion, dated Jul. 5, 2019, 13pgs.

(Continued)

*Primary Examiner* — Majid Jamialahmadi
(74) *Attorney, Agent, or Firm* — Innovation Counsel LLP

(57) ABSTRACT

The techniques of this disclosure generally relate to a vector flush sizing catheter that is used initially to disperse contrast and measure a length of a main vessel using radiopaque measuring markers of the catheter. Subsequently, the vector flush sizing catheter is used to guide and introduce another endovascular device into the main vessel. By using the vector flush sizing catheter for both procedures, the exchange of catheters, the complexity of the procedure, and the associated risks are minimized.

13 Claims, 5 Drawing Sheets

(51) Int. Cl.
*A61F 2/06* (2013.01)
*A61F 2/95* (2013.01)

(56) References Cited

U.S. PATENT DOCUMENTS

| | | |
|---|---|---|
| 9,320,503 B2 | 4/2016 | Bolduc |
| 2006/0100640 A1 | 5/2006 | Bolduc |
| 2008/0171934 A1 | 7/2008 | Greenan et al. |
| 2008/0255447 A1* | 10/2008 | Bourang ............. A61M 31/005 600/434 |
| 2009/0099650 A1 | 4/2009 | Bolduc et al. |
| 2009/0259296 A1 | 10/2009 | McIff et al. |
| 2014/0276602 A1* | 9/2014 | Bonnette ............... A61M 25/01 604/508 |
| 2015/0360002 A1* | 12/2015 | Pai ..................... A61B 5/02158 604/95.04 |
| 2016/0256120 A1* | 9/2016 | Stone .................... A61B 6/501 |
| 2018/0008801 A1* | 1/2018 | Solar ................ A61M 25/0068 |

OTHER PUBLICATIONS

Endovascular Management Solutions Brochure, Aortic Accessories Trifold, 2017, 6pgs.
Angiodynamics, Accu-Vu Sizing Catheter, 2018, 4pgs.
CN Application No. 2020-038658, Chinese Office Action, dated Nov. 29, 2021, 9 pages.

\* cited by examiner

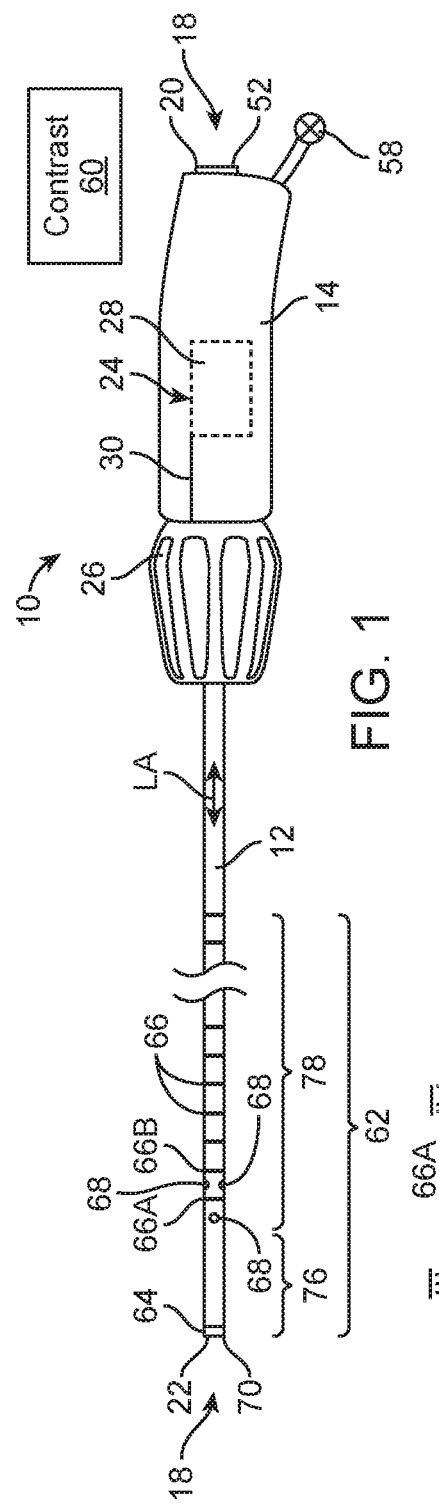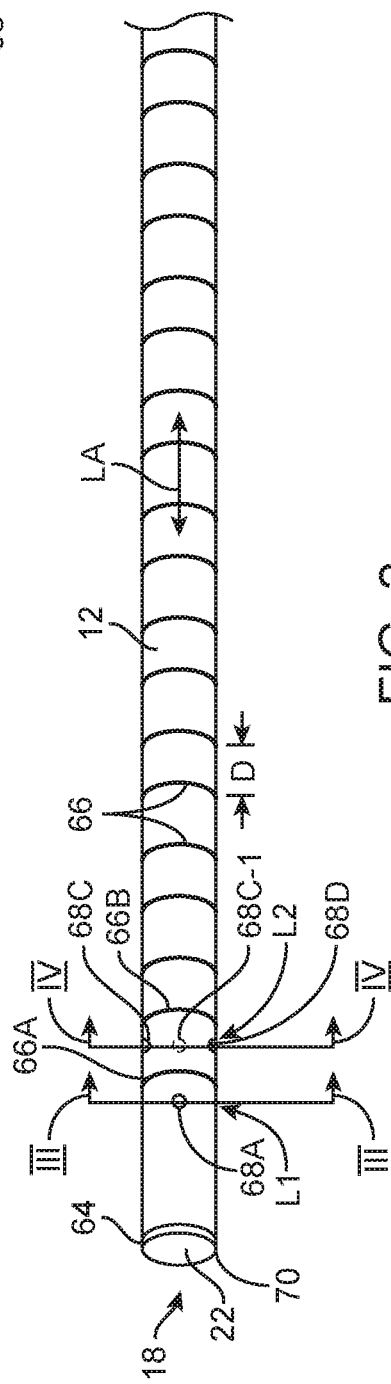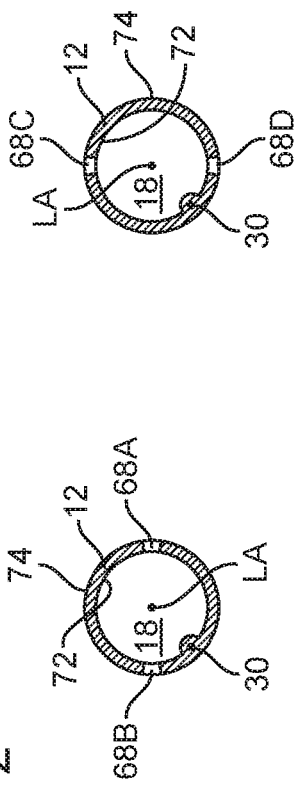

VECTOR FLUSH SIZING CATHETER AND METHOD

CROSS-REFERENCE TO RELATED APPLICATIONS

This application claims the benefit of U.S. Provisional Application No. 62/655,893, filed on Apr. 11, 2018, entitled "VECTOR FLUSH CATHETER OR ATG SIZING CATHETER" of Della Vecchia, which is incorporated herein by reference in its entirety.

FIELD

The present technology is generally related to an intra-vascular device and method. More particularly, the present application relates to a device for treatment of intra-vascular diseases.

BACKGROUND

A conventional stent-graft typically includes a radially expandable reinforcement structure, formed from a plurality of annular stent rings, and a cylindrically shaped layer of graft material defining a lumen to which the stent rings are coupled. Stent-grafts are well known for use in tubular shaped human vessels.

To illustrate, endovascular aneurysmal exclusion is a method of using a stent-graft to exclude pressurized fluid flow from the interior of an aneurysm, thereby reducing the risk of rupture of the aneurysm and the associated invasive surgical intervention.

To deploy the stent-graft, multiple exchanges of catheters are necessary. Each exchange includes the potential for blood loss, complicates the procedure, and takes time.

SUMMARY

The techniques of this disclosure generally relate to a vector flush sizing catheter that is used initially to disperse contrast and measure a length of a main vessel using radiopaque measuring markers of the catheter. Subsequently, the vector flush sizing catheter is used to guide and introduce another endovascular device into the main vessel. By using the vector flush sizing catheter for both procedures, the exchange of catheters, the complexity of the procedure, and the associated risks are minimized.

In one aspect, the present disclosure provides a catheter including a handle. A guide tube is coupled to the handle. A guide passage extends through the handle and through the guide tube. A steering assembly is configured to deflect a distal bendable part of the guide tube. At least one contrast flush hole is in a straight part of the guide tube.

In another aspect, the present disclosure provides a catheter including a handle. A guide tube is coupled to the handle. A guide passage extends through the handle and through the guide tube. A steering assembly is configured to deflect a distal bendable part of the guide tube. A plurality of regularly spaced apart radiopaque measuring markers are on a straight part of the guide tube.

In yet another aspect, the present disclosure provides a method including bending a distal bendable part of a guide tube of a catheter so that an opening at a distal end of the guide tube is directly adjacent at least one contrast flush hole in the guide tube. Contrast is dispersed through the opening and the at least one contrast flush hole. Radiopaque measuring markers on the guide tube are visualized. An endovascular device is guided through a guide passage of the guide tube.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 1 is a side view of a vector flush sizing catheter in accordance with one embodiment.

FIG. 2 is an enlarged perspective view of a distal portion of a guide tube of the vector flush sizing catheter of FIG. 1 in accordance with one embodiment.

FIG. 3 is a cross-sectional view of the guide tube along the line of FIG. 2 in accordance with one embodiment.

FIG. 4 is a cross-sectional view of the guide tube along the line IV-IV of FIG. 2 in accordance with one embodiment.

DETAILED DESCRIPTION

Figure 5:
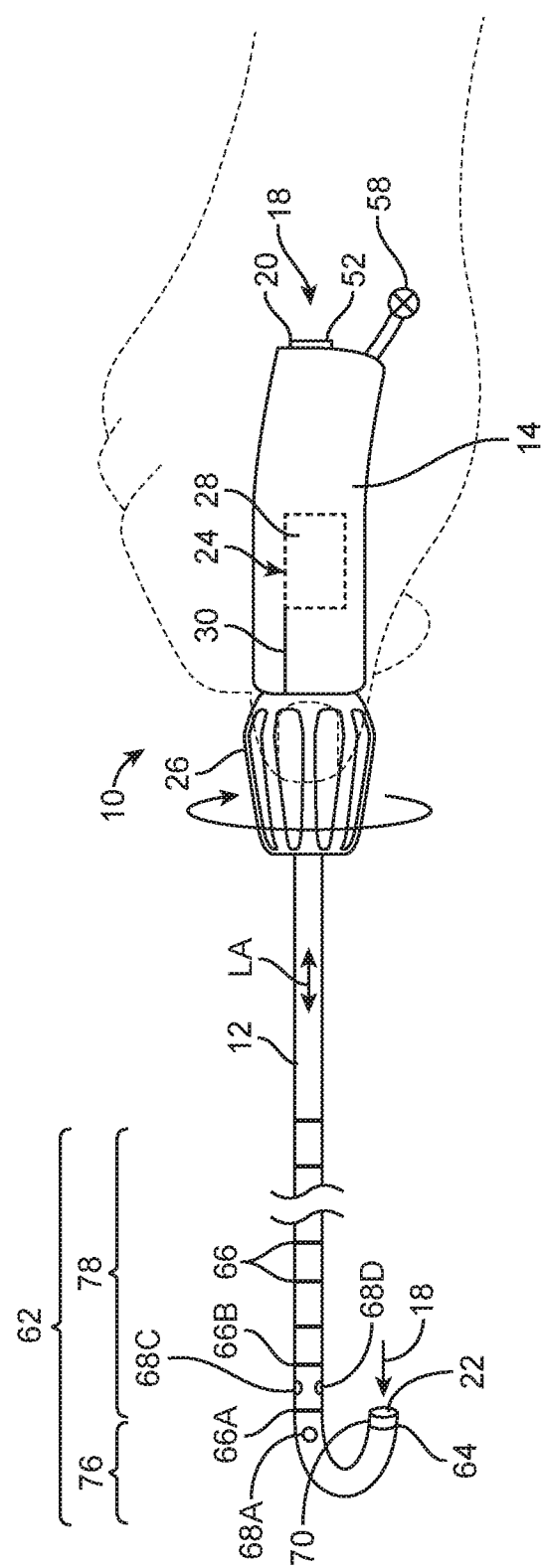
FIG. 5 is a side plan view of the vector flush sizing catheter with the guide tube deflected in accordance with one embodiment.

FIG. 1 is a side view of a vector flush sizing catheter 10 in accordance with one embodiment. Referring to FIG. 1, vector flush sizing catheter 10, sometimes called a steerable flushing sizing catheter 10, includes a flexible guide tube 12 carried by and coupled to a handle 14. Flexible guide tube 12 may be constructed, for example, by extrusion using standard flexible, medical grade plastic materials.

Handle 14 may be constructed, for example, from molded plastic. Handle 14 is sized to be conveniently held by a clinician, to introduce guide tube 12 into an interior body region that has been targeted for treatment.

Vector flush sizing catheter 10 includes an open path through which contrast can be delivered and an endovascular device or tool can be deployed for use. For this purpose, vector flush sizing catheter 10 includes an interior guide passage 18. Guide passage 18 extends through an interior portion of handle 14 continuously into and through guide tube 12. Entrance into guide passage 18 is provided by a proximal opening 20 formed in handle 14. Guide passage 18 terminates at an opening 22 at a distal end 70 of guide tube 12.

As used herein, the proximal end of a prosthesis is the end closest to the heart via the path of blood flow whereas the distal end is the end furthest away from the heart during deployment. In contrast and of note, the distal end of the catheter such as vector flush sizing catheter 10 is usually identified to the end that is farthest from the operator/handle 14 while the proximal end of the catheter is the end nearest the operator/handle 14.

For purposes of clarity of discussion, as used herein, the distal end of vector flush sizing catheter 10 is the end that is farthest from the operator (the end furthest from handle 14) while the distal end of the prosthesis is the end nearest the operator (the end nearest handle 14), i.e., the distal end of vector flush sizing catheter 10 and the proximal end of the prosthesis are the ends furthest from handle 14 while the proximal end of vector flush sizing catheter 10 and the distal end of the prosthesis are the ends nearest handle 14. However, those of skill in the art will understand that depending upon the access location, the prosthesis and vector flush sizing catheter 10 descriptions may be consistent or opposite in actual usage.

Guide tube 12, while flexible, suitably has a plastic memory or bias that normally orients the distal end region of guide tube 12 in an essentially straight configuration, as shown in FIG. 1. To enable greater control of the orientation of the distal end region of guide tube 10, vector flush sizing catheter 10 includes a steering assembly 24. In operation, steering assembly 24 deflects the distal end region of guide tube 12 out of its essentially straight configuration and into a bent or deflected configuration, as shown in FIG. 5 for example.

In its essentially straight configuration, guide tube 12 is well oriented for deployment into an interior body region, e.g., through an intra-vascular or cannulated access path. Upon deployment of guide tube 12 to a desired body region and/or during such deployment, a clinician can operate steering assembly 24 to deflect the distal end region of guide tube 12 in its bent or deflected condition.

Steering assembly 24 includes an actuator 26, a linkage system 28, and a deflecting component 30. Actuator 26 can be manipulated by the clinician. Actuator 26 is coupled through linkage system 28 to deflecting component 30, which is coupled to the distal end region of guide tube 12.

It should be appreciated that actuator 26 of steering assembly 24 can take many forms, such as a sliding lever or a pistol grip. Actuator 26 can be located at many locations on handle 14, such as the proximal end, the distal end, or the mid-portion. In the embodiment shown in FIG. 1, actuator 26 takes the form of a fluted knob that is rotationally attached to the distal end of handle 14. Actuator 26 is positioned so that it can be rotated by the thumb of the clinician's hand that holds handle 14.

In general operation, manual force applied by the clinician to actuator 26 is translated by linkage system 28 into a pulling force or tension exerted on deflecting component 30, which deflects or bends the distal end region of guide tube 12.

Vector flush sizing catheter 10 includes an in-line hemostatic valve assembly 52 at or near proximal opening 20 of passage 18. Valve assembly 52 prevents blood or fluid loss by sealing proximal opening 20 when an operative device or tool is within passage 18, as well as when no operative device or tool is present in passage 18.

An infusion valve 58 is also coupled to passage 18. In this way, fluid can be conveyed through passage 18 into the interior body region, e.g., to flush materials from passage 18 during use. In one embodiment, contrast 60 is introduced through infusion valve 58 and into passage 18 as discussed further below.

Although a particular structure deflecting or bending the distal end region of guide tube 12 is illustrated in FIG. 1 and discussed above, in light of this disclosure, those of skill in the art will understand that other deflecting or bending structures are used in other embodiments. Examples of suitable deflecting and bending structures are set forth in Bolduc, U.S. Pat. No. 9,320,503, issued Apr. 26, 2016, entitled "DEVICES, SYSTEMS, AND METHODS FOR GUIDING AN OPERATIVE TOOL INTO AN INTERIOR BODY REGION", which is herein incorporated by reference in its entirety. Also see the TourGuide™ steerable sheath sold by Medtronic, Minneapolis, Minn.

FIG. 2 is an enlarged perspective view of a distal portion 62 of guide tube 12 of vector flush sizing catheter 10 of FIG. 1 in accordance with one embodiment. FIG. 3 is a cross-sectional view of guide tube 12 along the line of FIG. 2 in accordance with one embodiment. FIG. 4 is a cross-sectional view of guide tube 12 along the line IV-IV of FIG. 2 in accordance with one embodiment.

Referring now to FIGS. 1, 2, 3 and 4 together, guide tube 12 includes a radiopaque distal end marker 64, a plurality of radiopaque measuring markers 66, and one or more contrast flush holes 68, sometimes called contrast flush openings or apertures.

Radiopaque distal end marker 64 is located at the very distal end 70 of guide tube 12 adjacent opening 22. Radiopaque distal end marker 64 permits fluoroscopic visualization of the orientation of distal end 70 of guide tube 12.

Radiopaque measuring markers 66 are regularly spaced apart radiopaque bands. Illustratively, each radiopaque measuring markers 66 is a complete circle extending around the circumference of guide tube 12 in a plane perpendicular to a longitudinal axis LA of guide tube 12.

In one embodiment, a fixed distance D between adjacent radiopaque measuring markers 66 is 1.0 cm although fixed distance D has other values in other embodiments depending upon the desired scale to be used. In other words, the pitch, i.e., the center to center spacing between adjacent radiopaque measuring markers 66, is equal to fixed distance D, e.g., 1 cm. In one particular embodiment, there are 20 radiopaque measuring markers 66 each spaced 1.0 cm apart and so radiopaque measuring markers 66 are sometimes called 20 gold marker bands spaced one centimeter apart. However, more or less radiopaque measuring markers 66 are used in other embodiments.

Radiopaque measuring markers 66, sometimes called gold marker bands 66, are formed of a radiopaque material, e.g., gold or other radiopaque material. Accordingly, radiopaque measuring markers 66 can be visualized using fluoroscopy. Radiopaque measuring markers 66 provide a ruler or measuring device to measure various anatomical features and various structures relative thereto as discussed further below.

Paying particular attention to FIGS. 3 and 4, contrast flush holes 68 extend from guide passage 18 within guide tube 12 through the entirety of guide tube 12 in the radial direction. More particularly, contrast flush holes 68 extend from an inner cylindrical surface 72 to an outer cylindrical surface 74 of guide tube 12. Contrast flush hole 68 allow contrast 60 to be flushed from guide passage 18 within guide tube 12 to the exterior of guide tube 12. As discussed above, contrast 60 is introduced into guide passage 18 through infusion valve 58.

In accordance with this embodiment, at any particular location along longitudinal axis LA of guide tube 12, there are more than one contrast flush hole 68, i.e., a plurality of contrast flush holes 68. More particularly, at a particular location along longitudinal axis LA, there is a pair of opposing contrast flush holes 68 opposite one another, i.e., at 180 degrees apart. However, in another embodiment, there is only a single contrast flush hole 68 at any particular location along longitudinal axis LA. In another embodiment, there are more than two, e.g., three or four, contrast flush holes 68 at any particular location along longitudinal axis LA.

Further, in accordance with this embodiment, one or more contrast flush holes 68 are located along longitudinal axis LA at two or more locations. For example, contrast flush holes 68 include four contrast flush holes 68A, 68B, 68C, and 68D. As illustrated in FIGS. 2, 3 and 4, at a first longitudinal location L1, there is a first pair of opposing contrast flush holes 68A, 68B and at a second longitudinal location L2, there is a second pair of opposing contrast flush holes 68C, 68D. Contrast flush holes 68A, 68B (first longitudinal location L1) are adjacent to and distal to the most distal radiopaque measuring marker 66A of radiopaque measuring markers 66. Radiopaque measuring marker 66A is sometimes called a first radiopaque measuring marker 66A.

Contrast flush holes 68C, 68D (second longitudinal location L2) are adjacent to and between first radiopaque measuring marker 66A and a second most distal radiopaque measuring marker 66B of radiopaque measuring markers 66. Radiopaque measuring marker 66B is sometimes called a second radiopaque measuring marker 66B and is directly adjacent and proximal to radiopaque measuring marker 66A. In one embodiment, there are one or more contrast flush holes 68 between first and second radiopaque measuring markers 66A and 66B.

In one embodiment, the radial orientation of contrast flush holes 68A, 68B is radially offset with the radial orientation of contrast flush holes 68C, 68D. For example, contrast flush holes 68A, 68B are radially offset by 90 degrees with respect to contrast flush holes 68C, 68D. Accordingly, in the view of FIG. 3, contrast flush holes 68A, 68B are horizontally aligned whereas in FIG. 4, contrast flush holes 68C, 68D are vertically aligned. By radially offsetting contrast flush holes 68, contrast 60 is locally dispersed regardless of the radial orientation of guide tube 12. Although a 90-degree radial offset is illustrated and discussed, in light of this disclosure, those of skill in the art will understand that contrast flush holes 68 can be radially offset with more or less than 90°.

In another embodiment, one or more, e.g., all, of contrast flush holes 68 are radially aligned. For example, as indicated by the dashed circle 68C-1 in FIG. 2, contrast flush holes 68A, 68B are radially aligned with contrast flush holes 68C-1, 68D.

In FIGS. 3 and 4, deflecting component 30 is illustrated as extending within a lumen of guide tube 12. Such an arrangement is simply illustrative, and deflecting component 30 and/or other structures can be routed to distal end 70 of guide tube 12 in other manners in other embodiments.

FIG. 5 is a side plan view of vector flush sizing catheter 10 with guide tube 12 deflected in accordance with one embodiment. As illustrated in FIG. 5, the clinician rotates actuator 26 to bend, sometimes called steer, a distal bendable part 76 of guide tube 12. In accordance with this particular embodiment, guide tube 12 is bent such that distal opening 22 is facing 180° as compared to guide tube 12 in the unbent (straight) configuration as illustrated in FIG. 1.

In one embodiment, distal bendable part 76 of guide tube 12 is distal to the distal most contrast flush holes 68, i.e., is distal to contrast flush holes 68A, 68B in this embodiment. Accordingly, contrast flush holes 68 and radiopaque measuring markers 66 are on a straight part 78 of guide tube 12. Although straight part 78 is illustrated and discussed as being straight, in light of this disclosure, those of skill in the art will understand that straight part 78 may be deflected or bent passing through the anatomy as discussed further below. Generally, distal portion 62 of guide tube 12 includes distal bendable part 76 and straight part 78 proximal to distal bendable part 76.

Further, once distal bendable part 76 is bent 180 degrees as illustrated in FIG. 5, distal opening 20 is longitudinally located adjacent to the first radiopaque marker 66A and between contrast holes 68. This allows contrast 60 to be dispersed from distal opening 20 and contrast holes 68 in a localized manner as discussed further below.

Figure 6:
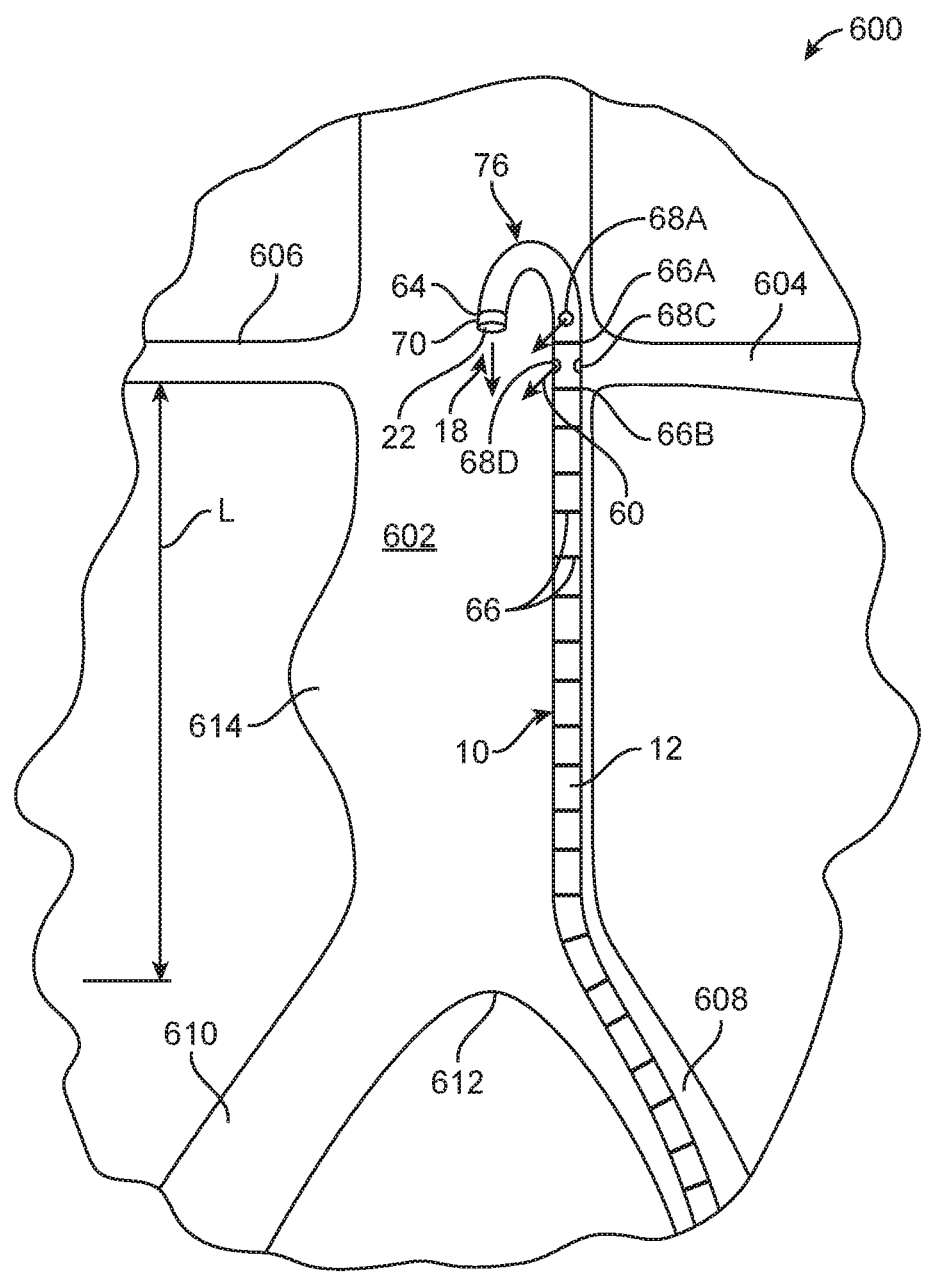
FIG. 6 is a partial cross-sectional view of a vessel assembly including the vector flush sizing catheter of FIG. 1 in accordance with one embodiment.

FIG. 6 is a partial cross-sectional view of a vessel assembly 600 including vector flush sizing catheter 10 of FIG. 1 in accordance with one embodiment. Vessel assembly 600 illustrates a series of vessels within the human body, including the aorta 602, the renal arteries 604, 606, and the common iliac arteries 608, 610. More particularly, the aorta 602, sometimes called a main vessel 602, descends from the renal arteries 604, 606, sometimes called branch vessels, 604, 606, to an aortic bifurcation 612 from which extend common iliac arteries 608, 610. Aortic bifurcation 612 is sometimes called a main vessel bifurcation 612.

In accordance with this example, aorta 602 includes an aneurysm 614, i.e., a diseased section of tissue.

Vector flush sizing catheter 10 is placed within aorta 602. Vector flush sizing catheter 10 is advanced into aorta 602, e.g., via the femoral artery via a femoral incision (not shown), in an unbent and straight state similar to that illustrated in FIG. 1.

In accordance with this embodiment, once contrast flush holes 68 are located adjacent renal arteries 604, 606, distal bendable part 76 is bent, e.g., 180 degrees, as discussed above. Accordingly, opening 22 and contrast flush holes 68 are located adjacent renal arteries 604, 606.

Once vector flush sizing catheter 10 is positioned where desired and distal bendable part 76 is bent, contrast 60 is dispersed from vector flush sizing catheter 10. As opening 22 is directly adjacent contrast flush holes 68, contrast 60 is dispersed with a high local concentration.

Disbursement of contrast 60 allows visualization of renal arteries 604, 606, aorta 602, aortic bifurcation 612 including common iliac arteries 608, 610 using fluoroscopy. Further, radiopaque measuring markers 66 are also visible using fluoroscopy. Radiopaque measuring markers 66 are used as a scale to determine the length L of aorta 602 between renal arteries 604, 606 and aortic bifurcation 612.

Figure 7:
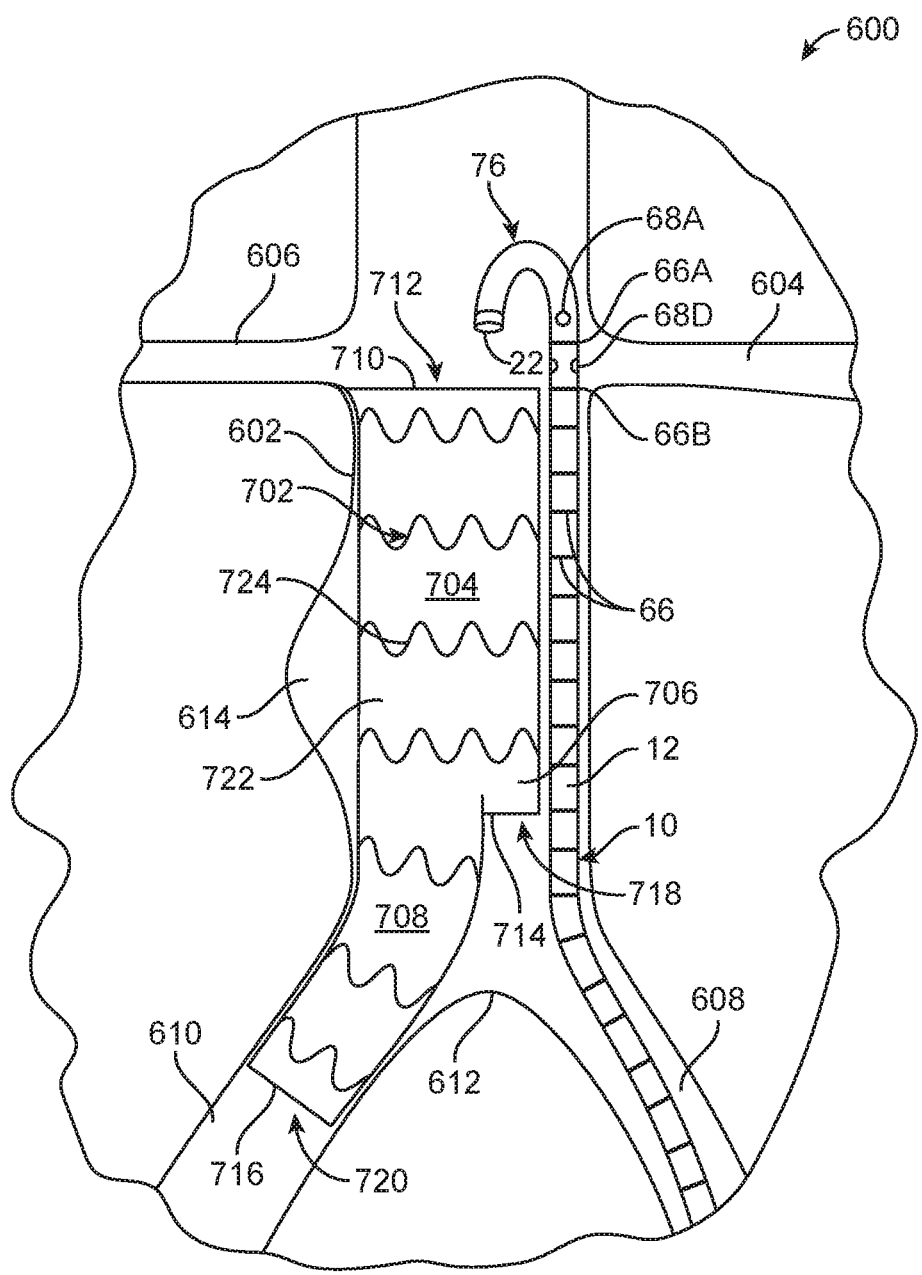
FIG. 7 is a partial cross-sectional view of the vessel assembly including the vector flush sizing catheter of FIG. 6 after deployment of an aortic bifurcated stent graft in accordance with one embodiment.

FIG. 7 is a partial cross-sectional view of vessel assembly 600 including vector flush sizing catheter 10 of FIG. 6 after deployment of an aortic bifurcated stent graft 702 in accordance with one embodiment. Aortic bifurcated stent graft 702 includes a main body 704, a short, e.g., first, leg 706, and a long, e.g., second, leg 708.

Main body 704 extends from a proximal end 710 of aortic bifurcated stent graft 702 to legs 706, 708. Main body 704 defines a main lumen 712. Short leg 706 extends from main body 704 to a distal end 714 of short leg 706. Long leg 708 extends from main body 704 to a distal end 716 of long leg 708. Legs 706, 708 define branch lumens 718, 720, respectively. Main lumen 712 is bifurcated into branch lumens 718, 720. Aortic bifurcated stent graft 702 includes graft material 722 and one or more stent rings 724.

In one embodiment, a plurality of aortic bifurcated stent grafts of different lengths are available to the clinician. Based upon the measurement of the length L of aorta 602 between renal arteries 604, 606 and aortic bifurcation 612 as measured using vector flush sizing catheter 10, a particular length aortic bifurcated stent graft 702 is selected.

Aortic bifurcated stent graft 702 is deployed adjacent and distal to renal arteries 604, 606 such that long leg 708 extends into common iliac artery 610. Aortic bifurcated stent graft 702 spans and thus excludes aneurysm 614. In one embodiment, vector flush sizing catheter 10 and/or contrast 60 dispersed therefrom facilitate accurate placement of aortic bifurcated stent graft 702.

Aortic bifurcated stent graft 702 is deployed such that vector flush sizing catheter 10 is located between aortic bifurcated stent graft 702 and the wall of aorta 602.

Figure 8:
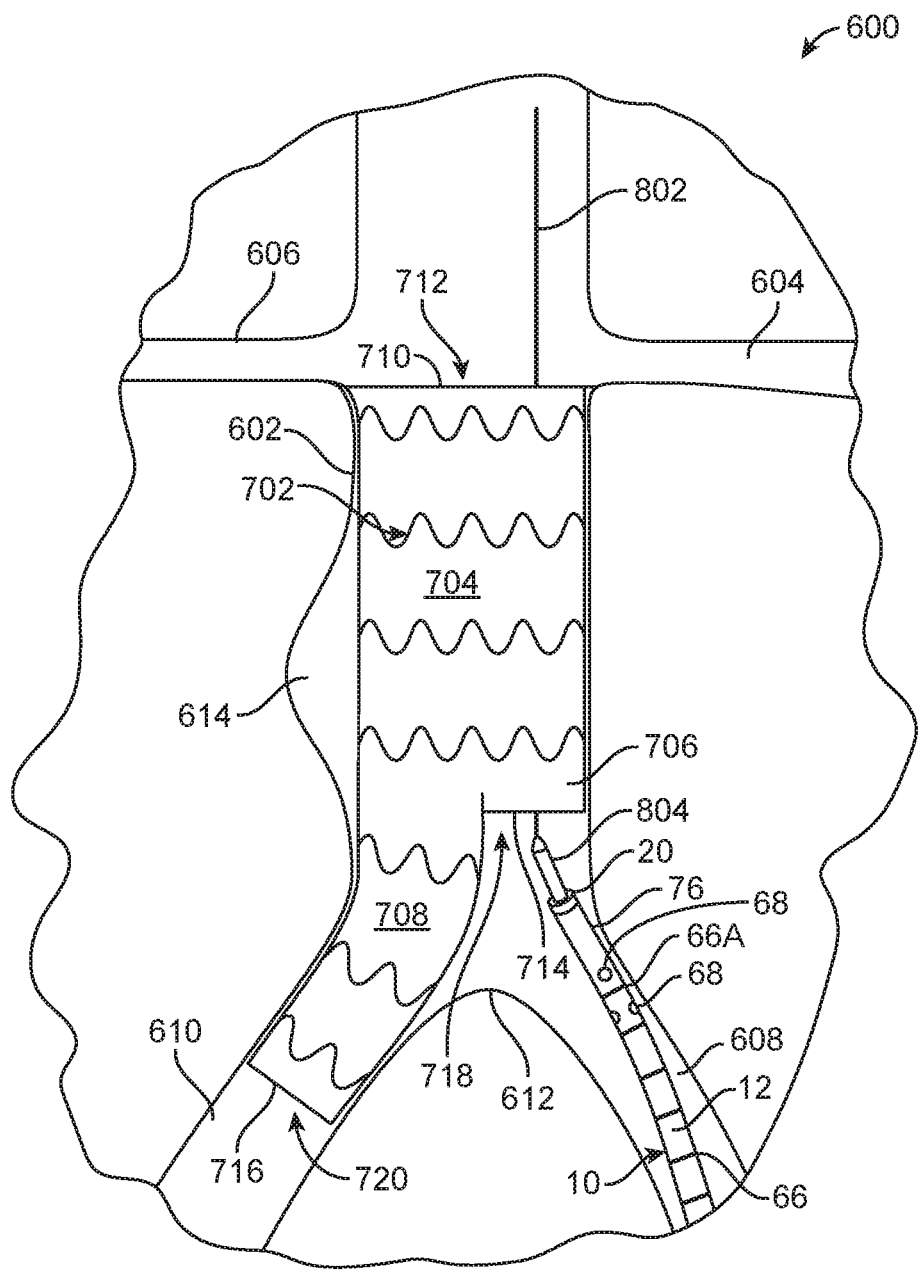
FIG. 8 is a partial cross-sectional view of the vessel assembly including the vector flush sizing catheter of FIG. 7 during deployment of a contralateral limb in accordance with one embodiment.

FIG. 8 is a partial cross-sectional view of vessel assembly 600 including vector flush sizing catheter 10 of FIG. 7 during deployment of a contralateral limb in accordance with one embodiment. Once aortic bifurcated stent graft 702 is deployed, distal bendable part 76 is again straightened as illustrated in FIG. 8. Vector flush sizing catheter 10 is withdrawn, sometimes called relocated, to be distal to distal end 714 of short leg 706. Vector flush sizing catheter 10 is then bent, sometimes called steered, to aim into distal end 714 and branch lumen 718 of short leg 706.

A guide wire 802 is advanced through vector flush sizing catheter 10, through short leg 706, and into/through main body 704. A delivery system 804 including a contralateral limb is advanced through vector flush sizing catheter 10 and over guide wire 802 into short leg 706. The contralateral limb is then deployed from delivery system 804 and within short leg 706 and common iliac artery 608. Delivery system 804, guidewire 802, and vector flush sizing catheter 10 are then removed.

As set forth above, vector flush sizing catheter 10 is used initially to disperse contrast 66 and measure the length L of aorta 602 between renal arteries 604, 606 and aortic bifurcation 612. After deployment of aortic bifurcated stent graft 702, vector flush sizing catheter 10 is used to guide and introduce another endovascular device, e.g., guidewire 802 and/or delivery system 804, into aorta 602. By using vector flush sizing catheter 10 for both procedures, the exchange of catheters, the complexity of the procedure, and the associated risks are minimized.

Although guidewire 802 and delivery system 804 are set forth as examples of endovascular devices, in other embodiments, vector flush sizing catheter 10 is used to steer and guide other endovascular devices such as endovascular anchors, branch stent graft, or other endovascular devices.

Further, vector flush sizing catheter 10 can be used for all Endovascular Aneurysm Repair (EVAR) and Thoracic Endovascular Aortic repair (TEVAR) procedures. Vector flush sizing catheter 10 is used by a physician as one catheter for the entire EVAR/TEVAR case versus multiple exchanges. Vector flush sizing catheter 10 can be used with all stent-grafts in addition to other vascular/IR procedures. There is potentially less blood loss, less catheter exchanges, and an easier procedure for the doctor. Also, there is the potential for quicker case times.

In one embodiment, vector flush sizing catheter 10 is 5 French (F), although other sizes such as 6 F, 6.5 F are used in other embodiments. This maximizes the anatomical applications for vector flush sizing catheter 10.

The length of vector flush sizing catheter 10 is 65 or 100 cm depending upon the anatomical location of desired use in one embodiment.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A catheter comprising:
    a handle;
    a guide tube coupled to the handle;
    a guide passage extending through the handle and through the guide tube;
    a steering assembly configured to deflect a distal bendable part of the guide tube;
    a radiopaque distal end marker at a very distal end of the distal bendable part of the guide tube; and
    a plurality of regularly spaced apart radiopaque measuring markers on a proximal straight part of the guide tube, wherein the radiopaque measuring markers comprise a first radiopaque measuring marker and an adjacent second radiopaque measuring marker, the first radiopaque measuring marker being the most distal radiopaque measuring marker of the plurality of radiopaque measuring markers, the catheter further comprising:
    at least one first contrast flush hole between the first radiopaque measuring marker and the second radiopaque measuring marker;
    at least one second contrast flush hole distal of all of the radiopaque measuring markers, wherein when the distal bendable part of the guide tube is bent 180 degrees, an opening at a distal end of the guide tube is longitudinally located adjacent the first radiopaque marker and between the at least one first contrast flush hole and the at least one second contrast flush hole; and
    wherein the distal bendable part has an absence of the plurality of radiopaque measuring markers.

2. The catheter of claim 1 wherein the at least one first contrast flush hole and the at least one second contrast flush hole extend from an inner surface to an outer surface of the guide tube.

3. The catheter of claim 1 wherein the at least one first contrast flush hole and the at least one second contrast flush hole extend from the guide passage through the entirety of the guide tube in a radial direction.

4. The catheter of claim 1 wherein the at least one first contrast flush hole comprises a plurality of contrast flush holes at a particular first longitudinal location along a longitudinal axis of the guide tube.

5. The catheter of claim 4 wherein the contrast flush holes are opposite one another.

6. The catheter of claim 4 wherein the at least one second contrast flush hole comprises a plurality of contrast flush holes at a second longitudinal location along the longitudinal axis of the guide tube.

7. The catheter of claim 1 wherein the at least one first contrast flush hole comprise a first pair of contrast flush holes at a first location along a longitudinal axis of the guide tube and the at least one second contrast flush hole comprises a second pair of contrast flush holes at a second location along the longitudinal axis.

8. The catheter of claim 7 wherein the first pair of contrast flush holes is radially offset from the second pair of contrast flush holes.

9. The catheter of claim 1 wherein each of the radiopaque measuring markers comprises a complete circle extending around a circumference of the guide tube in a plane perpendicular to a longitudinal axis of the guide tube.

10. The catheter of claim 1 wherein a fixed distance between each of the radiopaque measuring markers exists.

11. The catheter of claim 10 wherein the fixed distance equals 1 cm and there are twenty of the radiopaque measuring markers.

12. The catheter of claim 1 further comprising:
a guidewire within the guide passage; and
an endovascular device within the guide passage.

13. The catheter of claim 12 wherein the endovascular device comprises a delivery system comprising a contralateral limb.

* * * * *